United States Patent [19]

Negus

[11] Patent Number: 5,251,612
[45] Date of Patent: Oct. 12, 1993

[54] SELF-ALIGNING COUPLER FOR A LASER ENDOSCOPE

[75] Inventor: Charles C. Negus, Framingham, Mass.

[73] Assignee: Laser Engineering, Inc., Milford, Mass.

[21] Appl. No.: 791,469

[22] Filed: Nov. 13, 1991

[51] Int. Cl.$^5$ .............................................. A61B 1/06
[52] U.S. Cl. ............................................ 128/6; 606/13
[58] Field of Search .................. 606/2, 17, 18, 19, 13; 128/6, 4, 395; 385/117, 118, 33; 285/911, 24, 27, 184

[56] References Cited

U.S. PATENT DOCUMENTS

| | | | |
|---|---|---|---|
| 3,381,976 | 5/1968 | Goodson et al. | 285/911 X |
| 3,667,785 | 6/1972 | Kapeker | 285/911 X |
| 4,127,286 | 11/1978 | Albertsen | 285/911 X |
| 4,528,983 | 7/1985 | Erb | 606/18 |
| 4,597,380 | 7/1986 | Raif et al. | 128/6 |
| 4,611,888 | 9/1986 | Prenovitz et al. | 128/6 |
| 4,669,763 | 6/1987 | Phillips | 285/911 X |
| 4,917,083 | 4/1990 | Harrington et al. | 606/15 |
| 5,136,676 | 8/1992 | Arnett et al. | 128/4 X |

FOREIGN PATENT DOCUMENTS 2108227 5/1983 United Kingdom ............... 285/911

*Primary Examiner*—Richard J. Apley
*Assistant Examiner*—Karen A. Jalbert
*Attorney, Agent, or Firm*—Iandiorio & Dingman

[57] ABSTRACT

A self-aligning coupler for a laser endoscope having a body and a lumen extending from the body includes a coupler housing; an input port adapted for connection to a laser beam source; and an output port adapted for connection to the endoscope body; a tilt assembly; an alignment sleeve fixed to the tilt assembly for extending through the output port and the body into the lumen; lens means mounted with the tilt assembly for projecting the laser beam down the alignment sleeve and fixing the focus of the beam generally on the axis of the alignment sleeve; means for centering the sleeve with respect to the lumen and generally aligning the lumen and sleeve axes; and gap means between the tilt assembly and the coupler housing for enabling the tilt assembly to float in the coupler housing laterally relative to the axes of the sleeve and lumen for accommodating misalignment between the body and lumen while maintaining alignment of the lens means, sleeve and lumen.

13 Claims, 4 Drawing Sheets

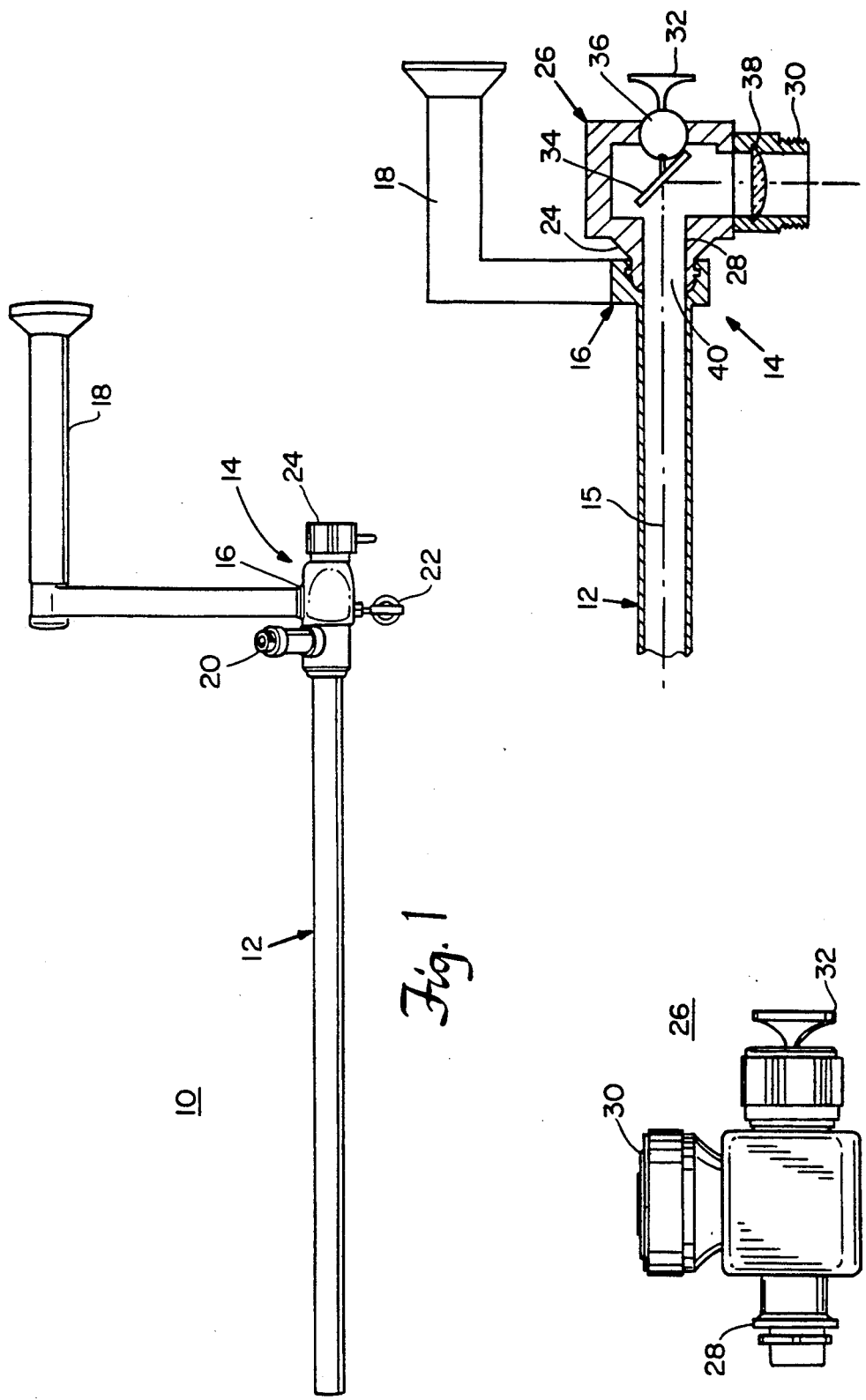

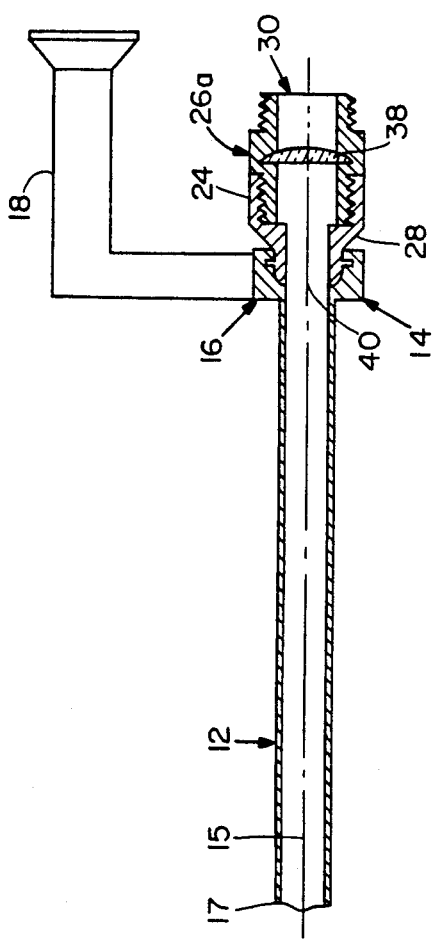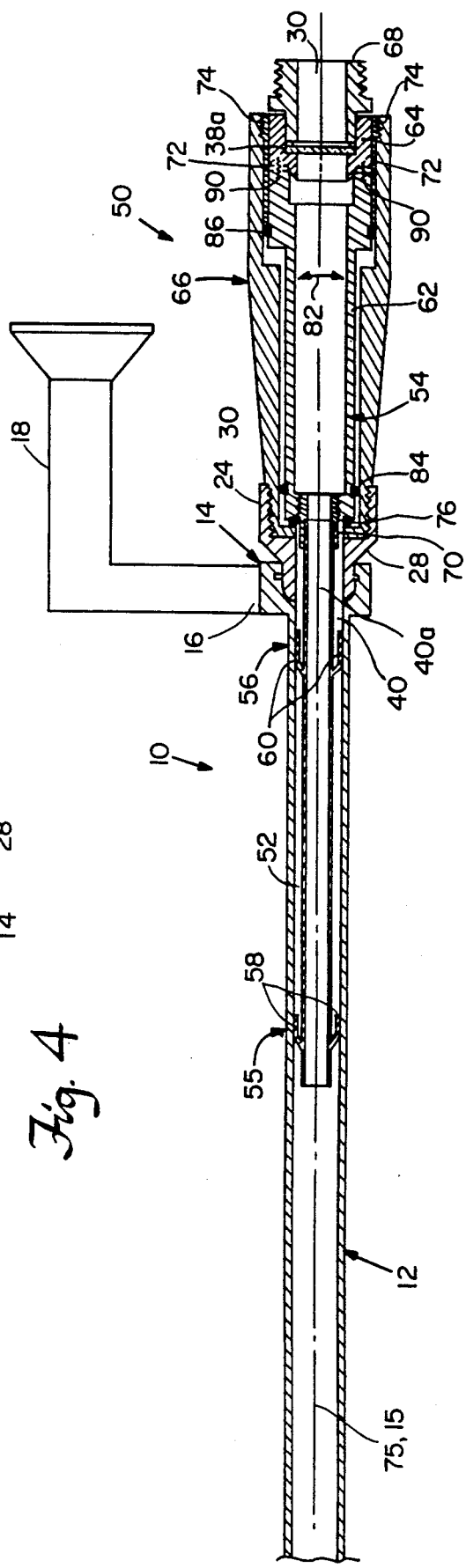

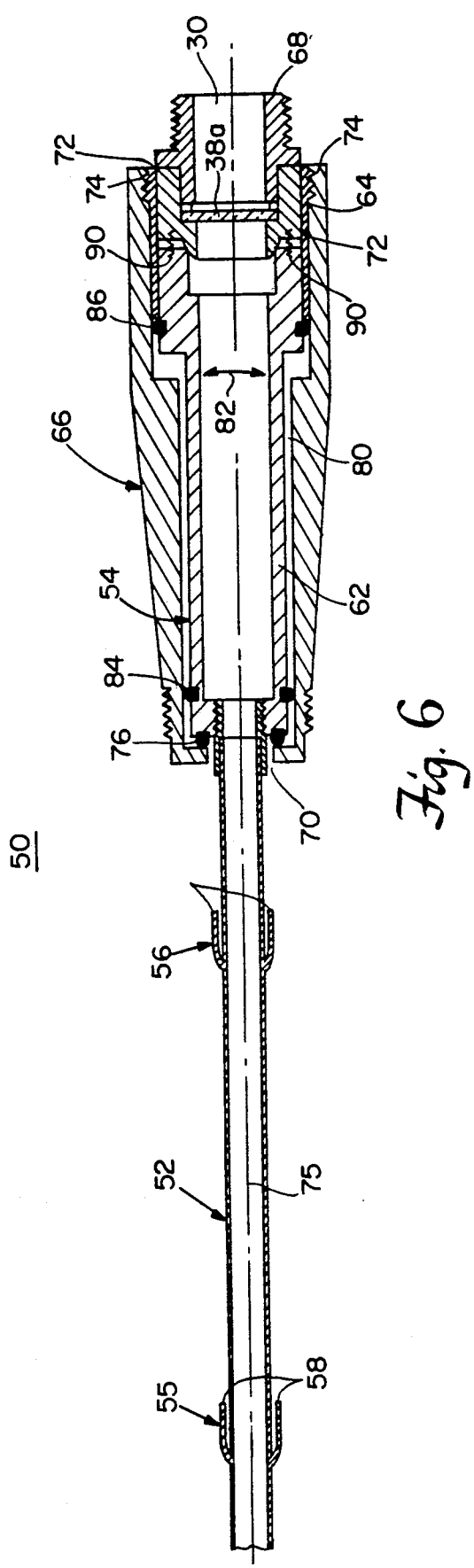
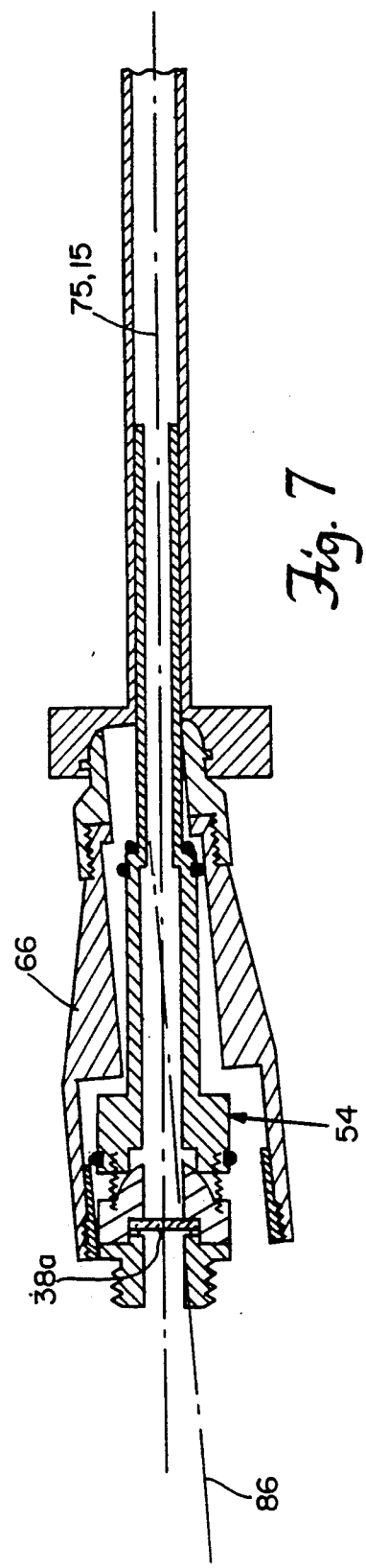

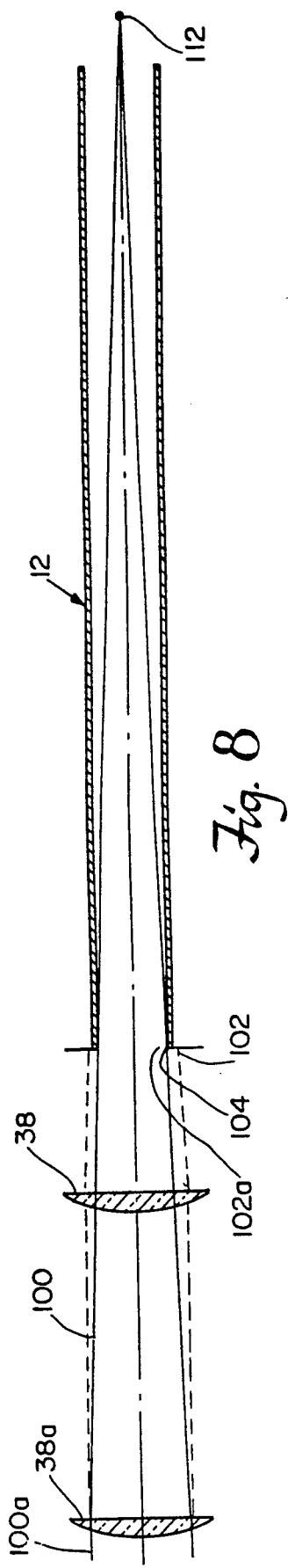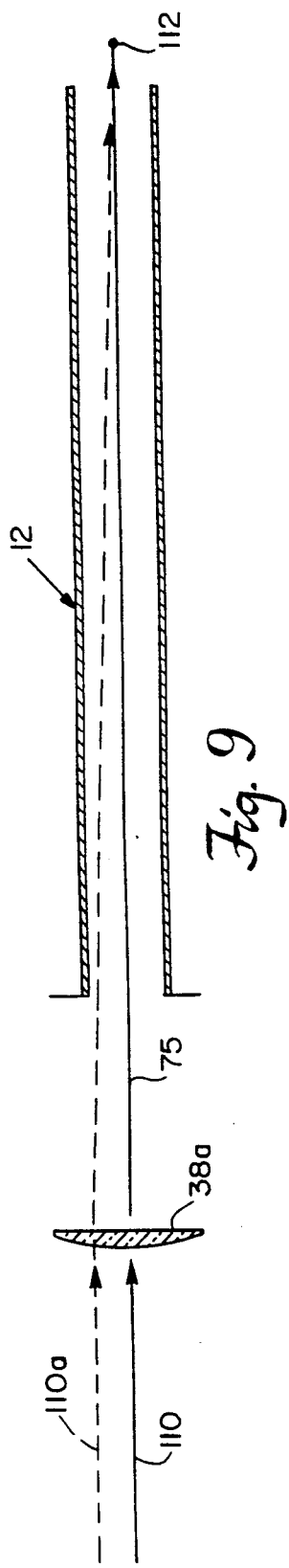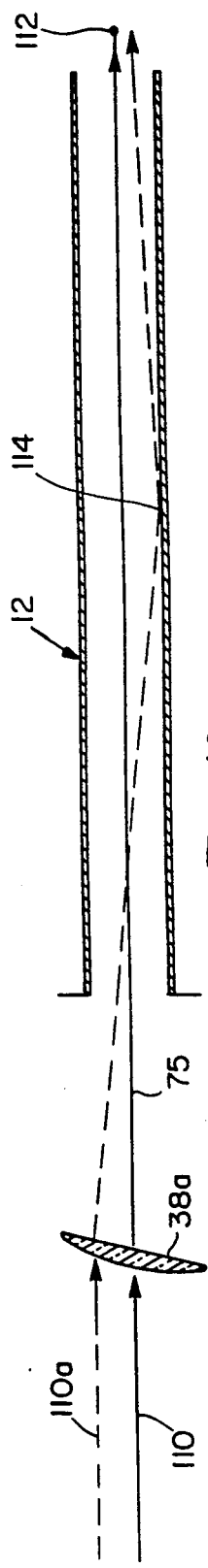

SELF-ALIGNING COUPLER FOR A LASER ENDOSCOPE

FIELD OF INVENTION

This invention relates to a self-aligning coupler for a laser endoscope.

BACKGROUND OF INVENTION

Conventional endoscopes include a main body from which the lumen extends. The body contains one port for viewing the operation site through the lumen, and another port for supplying to the operation site illumination through the lumen. Yet another port is provided for suction/purging and the primary port receives the tools or laser beam with which the surgery is to be performed. In laser surgery the end of the articulated arm through which the laser beam propagates is connected to the primary port through a coupler which may be a straight coupler or a joystick coupler. The joystick coupler can be difficult and frustrating to use because of the extreme sensitivity of the joystick in controlling the beam. The coupler contains a lens which focuses the laser beam at a focal point on the central axis of and somewhat beyond the distal end of the lumen. The coupler and lens are universal devices which do not provide precise alignment of the lens with the lumen. As a result the aiming of the surgical laser beam is difficult and significant power can be lost. Often the lens aperture is larger than the input to the lumen so light energy is lost before the beam enters the proximal end of the lumen. In addition, the lens can be misaligned. If the beam arrives on axis from the articulated arm there will be little inconvenience as the on-axis beam will still be focused on the lumen axis. However, if, as is more commonly the case, the beam arrives off-axis, the misaligned lens will establish a laterally offset focal point which will cause "wall bounce". That is, the beam will ricochet off the walls of the lumen and result in a defocused, fuzzy beam with a serious loss of intensity so that the requisite operating power is lost and precise aiming is frustrating if not impossible.

SUMMARY OF INVENTION

It is therefore an object of this invention to provide a self-aligning coupler for a laser endoscope.

It is a further object of this invention to provide such a self-aligning coupler which eliminates loss of laser power due to mismatched apertures between the coupling lens and lumen.

It is a further object of this invention to provide such a self-aligning coupler which eliminates loss of laser power due to misalignment between the laser beam, coupler and lumen.

It is a further object of this invention to provide such a self-aligning coupler which eliminates loss of laser power due to misalignment between the coupler, lens and lumen.

It is a further object of this invention to provide such a self-aligning coupler which accommodates any articulated laser arm without adjustment or realignment.

It is a further object of this invention to provide such a self-aligning coupler which eliminates "wall bounce".

It is a further object of this invention to provide such a self-aligning coupler which eliminates the need for a joystick coupler and joystick control.

The invention results from the realization that an improved universal coupler which can interconnect any endoscope and laser source and which is completely self-aligning despite misalignment of the body and lumen can be achieved with an alignment sleeve centered in the lumen and the laser beam focusing lens mounted in a support fixed to the sleeve yet free to float relative to the body of the endoscope.

This invention features a self-aligning coupler for a laser endoscope which includes a body and a lumen extending therefrom. The self-aligning coupler includes a coupler housing; an input port adapted for connection to a laser beam source; and an output port adapted for connection to an endoscope body. There is a tilt assembly and an alignment sleeve is fixed to the tilt assembly for extending through the output port and the body into the lumen. Lens means are mounted with the tilt assembly for projecting the laser beam down the alignment sleeve and fixing the focus of the beam generally on the axis of the alignment sleeve. There are means for centering the sleeve with respect to the lumen and generally aligning the lumen and sleeve axes. Gap means between the tilt assembly and the coupler housing enable the tilt assembly to float in the coupler housing laterally relative to the axes of the sleeve and lumen for accommodating misalignment between the body and lumen while maintaining alignment of the lens means, sleeve and lumen.

In a specific embodiment, the tilt assembly may include a tilt barrel, a tilt mount and the input port. The lens means may be mounted in the tilt mount. The lens means may be disposed proximate the input port end of the coupler housing. The tilt assembly may further include means for setting the orientation of the tilt mount and lens means relative to the tilt barrel. The means for centering may include spacer means disposed between the sleeve and lumen. The spacer means may be fixed to the sleeves and they may be resilient. There may be resilient means in the gap means for floating the tilt assembly and the coupler housing relative to each other. The resilient means may be fixed to the tilt assembly and they may include at least one resilient element proximate the input port end of the coupler housing. The resilient means may also include at least one resilient element proximate the output port end of the coupler housing. The coupler housing may include retainer means for accurately securing the tilt assembly toward the output port end of the coupler housing.

DISCLOSURE OF PREFERRED EMBODIMENT

Other objects, features and advantages will occur to those skilled in the art from the following description of a preferred embodiment and the accompanying drawings, in which:

FIG. 1 is a side elevational view of an endoscope usable with the self-aligning coupler according to this invention;

FIG. 2 is an elevational view of a conventional joystick coupler that may be used with the endoscope of FIG. 1;

FIG. 3 is an enlarged sectional schematic view of the joystick coupler of FIG. 2 mounted on the endoscope of FIG. 1;

FIG. 4 is a view similar to FIG. 3 where the coupler is a conventional straight coupler instead of the joystick coupler of FIG. 3;

FIG. 5 is a self-aligning coupler according to this invention installed in an endoscope;

FIG. 6 is an enlarged, more detailed view of the self-aligning coupler of FIG. 5;

FIG. 7 is a view similar to FIG. 5 showing the accommodation of the self-aligning coupler of this invention for misalignment between the body and lumen of a conventional endoscope;

FIG. 8 is a schematic diagram illustrating the loss of laser beam energy due to mismatch of the apertures between the lumen and laser beam focusing lens;

FIG. 9 is a view similar to FIG. 8 illustrating the focusing response of a laser beam focusing lens with an on-axis and off-axis laser beam; and FIG. 10 is a view similar to FIG. 9 showing the function of the laser beam focusing lens on an off-axis laser beam when the lens is misaligned with the lumen.

The invention may be accomplished with a self-aligning coupler for a laser endoscope, which endoscope includes a body and a lumen extending therefrom. There is a coupler housing, typically in the form of a cylindrical or barrel shape, having an output port adapted for connection to the endoscope body. There is a tilt assembly which resides in the coupler housing, and an alignment sleeve which is fixed in the tilt assembly and extends through the output port of the coupler housing and the body of the endoscope into the lumen. There is an input port adapted for connection to a laser beam source such as an articulated arm, connected to the tilt mount on the tilt assembly. There are lens means mounted with the tilt assembly for projecting the laser beam down the alignment sleeve and fixing the focus of the beam generally on the axis of the alignment sleeve. There are means for centering the sleeve with respect to the lumen and generally aligning the lumen and sleeve axes. Gap means between the tilt assembly and the coupler housing enable the tilt assembly to float in the coupler housing laterally relative to the axes of the sleeve and lumen for accommodating misalignment between the body and lumen while maintaining alignment of the lens means, sleeve and lumen. Generally, the various parts are axially symmetrical, having generally rotational symmetry, and the various axes are generally concentric. The tilt assembly is formed from a tilt barrel and a tilt mount. The lens is mounted in the tilt mount and there are means such as spaced adjustment screws for setting the orientation of the tilt mount and lens relative to the tilt barrel. Once set, the lens is fixed in position and will maintain its alignment with the sleeve. The sleeve may be centered in the lumen by means of spacers disposed between the sleeve and lumen. The spacers may be fixed to either one of the sleeve or the lumen, or some may be fixed to each. The spacers may be resilient. The gap may include resilient members for floating the tilt assembly and the coupler housing relative to each other. The resilient members may be fixed to one or the other or both the tilt assembly and coupler housing. There may be at least one resilient element proximate the input port end of the coupler housing and there may be one proximate the output end of the coupler housing. The coupler housing may include retainer means for axially securing the tilt assembly toward the output end of the coupler housing.

There is shown in FIG. 1 a conventional endoscope 10 including lumen 12 and body 14. Body 14 has one port 16 for interconnecting with the eyepiece 18 through which the surgeon can view through lumen 12 the interior of the body cavity on which the surgery is to be carried out. Another port 20 carries illumination down through lumen 12 to the area to be viewed. A third port 22 is used for smoke evacuation, insuflation, and/or purging of the lumen, and the primary port 24 is used to interconnect to a laser beam source such as an articulated arm and coupler which carries the laser beam from the laser, or other surgical instruments.

In practice, connected to port 24 is a coupler such as joystick coupler 26, FIG. 2, which includes a connector 28 for engaging port 24, port 30 for receiving the laser beam source, and a joystick 32 which can be wiggled by the thumb of the surgeon to control the location of the beam. Typical joystick coupler 26 includes a steering mirror 34, FIG. 3, controlled through ball joint 36 operated by joystick 32. A lens 38 focuses the laser beam received at port 30, for example from an articulated arm interconnected with the laser source. A less complicated conventional coupler, straight coupler 26a, FIG. 4, eliminates joystick 32, ball joint 36 and mirror 34 and includes simply the laser beam focusing lens 38. Since lens 38 is quite close to the entrance aperture 40 of lumen 12 in FIGS. 3 and 4, a problem arises in that the exit aperture of the lens 38 is larger than the entrance aperture of lumen 40 and thus significant laser beam energy is lost before it even enters lumen 12. In addition, since the body 14 and lumen 12 are neither made nor assembled with the precision required in laser systems, misalignments between the lumen 12, the body 14 and lens 38 can cause further losses through misalignment and "wall bounce". Ideally, lens 38, FIGS. 3 and 4, focuses the laser beam along the axis 15 of lumen 12, but this cannot always be effected since housing 14 and lumen 12 are not always precisely aligned and thus off-axis laser beams incident on lens 38 result in a focal point which while properly beyond the tip 17 of lumen 12 is not on axis 15 and thus causes "wall bounce", resulting in a fuzzy, defocused laser beam whose location is difficult to fix and whose intensity is often too low to effect the desired surgical operation.

In accordance with this invention, a self-aligning coupler 50, shown in FIG. 5 installed in a typical endoscope and shown in FIG. 6 separately and enlarged, includes an alignment sleeve 52 which is fixed to a tilt assembly 54. The various structures for viewing, illuminating, purging/suction in lumen 12 have been omitted for purposes of clarity. Alignment sleeve 52 includes one or more centering devices 55, 56, each of which may include two or more spacers 58, 60. Tilt assembly 54 includes a tilt barrel or housing 62 and a tilt mount 64 in which is installed laser beam focusing lens 38a.

Tilt assembly 54 includes an inlet port 30 for connection to a laser beam source such as an articulated arm, and is mounted in coupler housing or barrel 66 which includes an outlet port 70 that interconnects with the primary port 24 of endoscope 10. An alignment sleeve 52 extends through outlet port 70 into lumen 12. It extends at least part way down the longitudinal extent of lumen 12. Retainer ring 72 engages with threads 74 on the inside of coupler housing 66 and secures tilt assembly 54 toward outlet port 70, where "O" ring 76 resiliently interconnects tilt assembly 54 and outlet port 70 of coupler housing 66. Retainer ring 72 urges the tilt assembly toward the output port 70 along axis 75 of alignment sleeve 52 and tilt housing 54. A gap 80 is defined between tilt assembly 54 and coupler housing 66 to enable the housing to move laterally as indicated by arrow 82 with respect to the axis 75 of sleeve 52.

Resilient means such as "O" ring 84 and "O" ring 86 may be provided to provide a snug and quiet yet resilient engagement between tilt housing 54 and coupler housing or barrel 66. "O" rings 76, 84, 86 are each housed in recesses in tilt assembly 54, but this is not a necessary limitation of the invention, and of course the resilient means need not be "O" ring but may be spaced resilient members such as springs or elastomeric material. Threaded cap 68 encloses the end of tilt assembly 54 and carries in it the inlet port 30.

The tilt barrel 62 and tilt mount 64 are interconnected by a number of set screws 90 which can be adjusted to move tilt mount 64 with respect to tilt barrel 62 so as to precisely orient lens 38a so that the laser beam is focused on axis 75. Once this is done the orientation of lens 38a is fixed with respect to tilt barrel 62 and sleeve 52 so that no further misalignment can occur. Moreover, since sleeve 52 is held snugly within lumen 12, the laser beam focus is precisely located on the axis 75 of sleeve 52 generally coincident with axis 15 of lumen 12. And regardless of whether or not the laser beam is on-axis or off-axis, it is always focused on axis 75 because lens 38a always remains precisely oriented with respect to axis 75 of sleeve 52, even if it is off-axis as it appears at lens 38a.

If, as is often the case, the coupler body 14 is misaligned with respect to its own lumen 12, this does not affect the alignment of the system, for according to this invention sleeve 52 is generally centered in lumen 12 and the ability of tilt assembly 54 to float in coupler housing 66 means that tilt assembly 54, and so lens 38a, maintain their alignment with sleeve 52 at its axis 75 as well as axis 15 of lumen 12 regardless of how misaligned may be the relationship of body 14 and lumen 12. A typical misalignment is illustrated in FIG. 7, where the axes 75 and 15 of the sleeve 52, lumen 12 and the tilt assembly 54 are all properly aligned, but the axis 86 of coupler housing 66 is skewed. Note, however, that though coupler housing 66 and its axis 86 are skewed, tilt assembly 54 is free to assume the proper position to maintain the alignment of mirror 38a with the axes 75 and 15.

The improvement effected by moving lens 38a farther away from the input end of the lumen 12 can be seen in FIG. 8, where laser beam 100, shown in phantom, incident on lens 38a, results in an aperture 102 which is larger than the aperture 104 of lumen 12. By moving the lens back to the position of lens 38a, laser beam 100a converges to a much smaller aperture 102a, which is well within the aperture 104 of lumen 12, so that no laser beam energy is lost.

The effectiveness of the floating tilt assembly, which permits lens 38a to stay aligned with sleeve 52 and lumen 12, is shown in FIGS. 9 and 10. When lens 38a is properly oriented and on-axis with respect to axis 75, a laser beam 110, properly centered, is easily focused on axis 75 at point 112. So too is an off-axis laser beam 110a. However, when lens 38a is improperly oriented, FIG. 10, with respect to axis 75, the off-axis laser beam 110a does not focus at point 112 but rather is directed at the wall of lumen 12, where it impinges for example at 114, causing "wall bounce", which results in scattering of the laser light, a fuzzy, defocused beam, and a significant loss of energy.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A self-aligning coupler for a laser endoscope having a body and a lumen extending therefrom, comprising:
a coupler housing; an input port adapted for connection to a laser beam source; and an output port adapted for connection to the endoscope body; a tilt assembly within said coupler housing; an alignment sleeve fixed to said tilt assembly for extending through said output port and body into said lumen; lens means mounted with the tilt assembly for projecting the laser beam down said alignment sleeve and fixing the focus of the beam generally on the axis of said alignment sleeve; means for centering said sleeve with respect to said lumen and generally aligning said lumen and sleeve axes; and gap means between said tilt assembly and said coupler housing for enabling said tilt assembly to float in the coupler housing laterally relative to the axes of said sleeve and lumen for accommodating misalignment between the body and lumen while maintaining alignment of said lens means, sleeve and lumen.

2. The self-aligning coupler for a laser endoscope of claim 1 in which said tilt assembly includes a tilt barrel and a tilt mount.

3. The self-aligning coupler for a laser endoscope of claim 2 in which said lens means is mounted in said tilt mount.

4. The self-aligning coupler for a laser endoscope of claim 3 in which said tilt assembly further includes means of resetting the orientation of said tilt mount and lens means.

5. The self-aligning coupler for a laser endoscope of claim 1 in which said lens means is disposed proximate the input port end of said coupler barrel.

6. The self-aligning coupler for a laser endoscope of claim 1 in which said means for centering includes spacer means disposed between said sleeve and lumen.

7. The self-aligning coupler for a laser endoscope of claim 6 in which said spacer means are fixed to said sleeve.

8. The self-aligning coupler for a laser endoscope of claim 6 in which said spacer means are resilient.

9. The self-aligning coupler for a laser endoscope of claim 1 further including resilient means in said gap means for floating said tilt assembly and said coupler housing relative to each other.

10. The self-aligning coupler for a laser endoscope of claim 9 in which said resilient means are fixed to said tilt assembly.

11. The self-aligning coupler for a laser endoscope of claim 9 in which said tilt assembly includes at least one resilient element proximate the input port end of the coupler housing.

12. The self-aligning coupler for a laser endoscope of claim 9 in which said tilt assembly includes at least one resilient element proximate the output port end of the coupler housing.

13. The self-aligning coupler for a laser endoscope of claim 1 in which said coupler housing includes retainer means for axially securing said tilt assembly toward the output port end of said coupler housing.

* * * * *